US00PP24799P2

(12) United States Plant Patent
de Bont

(10) Patent No.: US PP24,799 P2
(45) Date of Patent: Aug. 19, 2014

(54) ***ECHINACEA* PLANT NAMED 'PIPAS'**

(50) Latin Name: ***Echinacea* hybrid**
Varietal Denomination: Pipas

(71) Applicant: Dionysius F. M. de Bont, Gouda (NL)

(72) Inventor: Dionysius F. M. de Bont, Gouda (NL)

( * ) Notice: Subject to any disclaimer, the term of this patent is extended or adjusted under 35 U.S.C. 154(b) by 0 days.

(21) Appl. No.: 13/986,124

(22) Filed: Apr. 3, 2013

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — June Hwu
*Assistant Examiner* — Keith Robinson
(74) *Attorney, Agent, or Firm* — Penny J. Aguirre

(57) ABSTRACT

A new cultivar of hybrid *Echinacea*, 'Pipas', characterized by its inflorescences with red-orange cones with numerous ray florets that are held horizontal and open bright pink-red and mature to dark pink, its strong stems with numerous inflorescences, and its plant height of 50 to 55 cm.

2 Drawing Sheets

Botanical classification: *Echinacea* hybrid.
Variety denomination: 'Pipas'.

BACKGROUND OF THE INVENTION

The present invention relates to a new and distinct cultivar of *Echinacea* of hybrid origin and will be referred to hereafter by its cultivar name, 'Pipas'. 'Pipas' represents a new coneflower, an herbaceous perennial grown for landscape use.

The Inventor selected the new cultivar, 'Pipas', in a seedbed at a nursery in Sint Annaland, The Netherlands in August of 2008. The seedbed had been planted with seeds collected and pooled from unnamed proprietary plants of *Echinacea purpurea* and unnamed proprietary plants of hybrid *Echinacea*. The exact parents are therefore unknown.

Asexual propagation of the new cultivar was first accomplished by in vitro propagation under the direction of the Inventor in Rijswijk, The Netherlands in September of 2010. Asexual propagation by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pipas' as a unique cultivar of *Echinacea*.

1. 'Pipas' exhibits inflorescences with red orange cones and ray florets that are uniquely colored; opening bright pink-red and maturing to dark pink.
2. 'Pipas' exhibits numerous ray florets that are held horizontal.
3. 'Pipas' exhibits strong stems with multiple inflorescences per stem.
4. 'Pipas' reaches a height of 50 to 55 cm in height.

The new cultivar can be most closely compared to the cultivars 'Meditation' (US 2013/0219578P1) and 'CBG Cone2' (U.S. Plant Pat. No. 18,839). 'Meditation' is similar to 'Pipas' in having pinkish pink florets, however 'Meditation' differs from 'Pipas' in having ray florets that are turn lighter pink as they age, a disk head that is more globular in shape, and in being shorter in height. 'CBG Cone2' is similar to 'Pipas' in ray floret color, however 'CBG Cone2' differs from 'Pipas' in having ray florets that are less numerous, less inflorescences per stem and in being slightly shorter in height.

BRIEF DESCRIPTION OF THE DRAWINGS

The plants in the accompanying photographs depict the characteristics of a two year-old plant of 'Pipas' as field grown in Sint Annaland, The Netherlands and placed in a two-gallon container for the photographs.

The photograph in FIG. 1 provides a side view of a plant in bloom.

Figure 1:
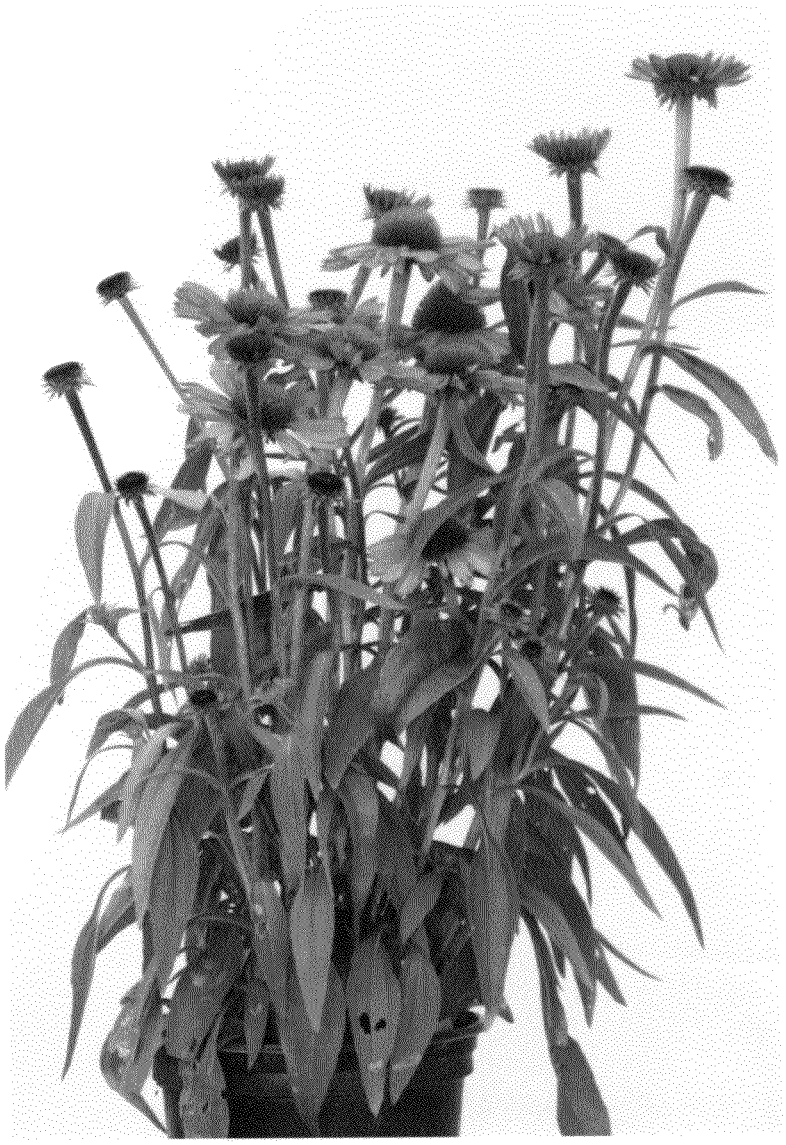
Figure 2:
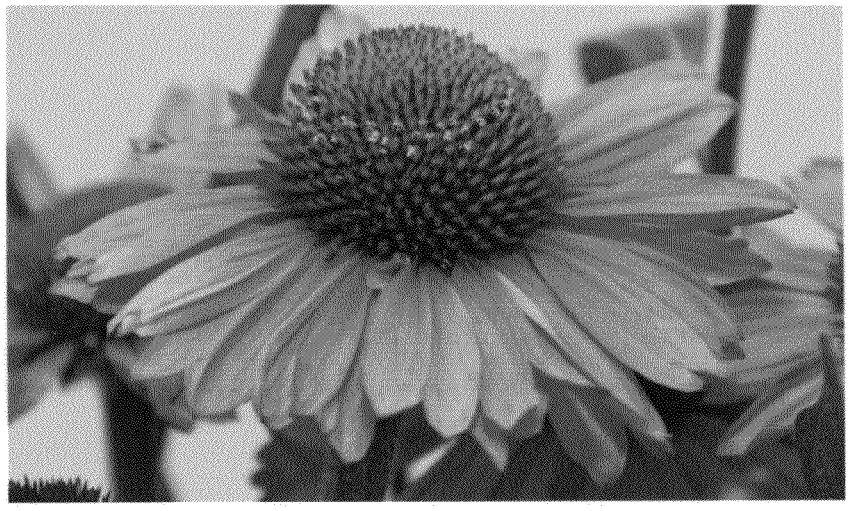

The photograph in FIG. 2 provides a close-up view of an inflorescence of 'Pipas'.

Figure 3:
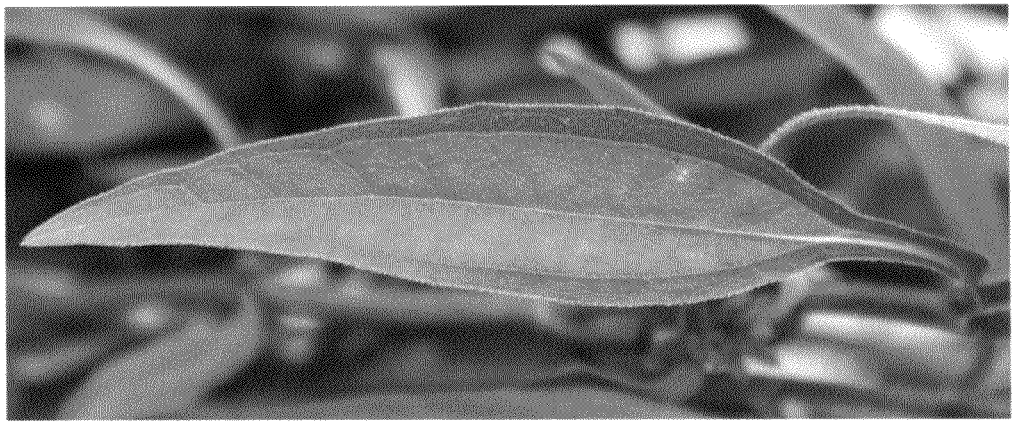

The photograph in FIG. 3 provides a close-up view of a leaf of 'Pipas'. The colors in the photograph may differ slightly from the color values cited in the detailed botanical description, which accurately describe the colors of the new *Echinacea*.

BOTANICAL DESCRIPTION OF THE PLANT

The following is a detailed description of six month-old plants of 'Pipas' as field grown in Sint Annaland, The Netherlands. Plants were grown under average day temperatures ranging from 15° to 32° C. and average night temperatures of 12° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From July into September in The Netherlands.

*Plant type*.—Herbaceous perennial.

*Plant habit*.—Clump forming, upright with strong branched flowering stems.

*Height and spread*.—Reaches 50 to 55 cm in height and an average of 35 cm in spread.

*Cold hardiness*.—At least to U.S.D.A. Zones 3.

*Diseases and pests*.—Not more susceptible to pests or diseases than other *Echinacea* varieties.

*Root description*.—Fibrous.

*Propagation*.—Tissue culture.

*Growth rate*.—Moderately vigorous.

Stem description:

*Shape*.—Rounded.

*Stem color*.—144A, marbled with 143A.

*Stem size*.—Average of 5 mm in diameter and an average of 29.3 cm in height.

*Stem surface*.—Slightly rough to the touch due to being densely covered with very short strigose hairs; 1 mm in length and NN155D in color.

*Stem strength*.—Strong.

*Stem number*.—Average of 15 main stems.

*Branching*.—Un-branched.

Foliage description:

*Leaf shape*.—Narrow ovate.

*Leaf division*.—Simple.

*Leaf base*.—Attenuate.

*Leaf apex*.—Long acute.

*Leaf venation*.—Pinnate, upper surface color; between 137B and 143A, lower surface color 143A.

*Leaf margins*.—Entire to coarsely and shallowly dentate.

*Leaf attachment*.—Petiolate.

*Leaf arrangement*.—Alternate.

*Internode length*.—An average of 3.7 cm.

*Leaf size*.—Average of 9.9 cm in length and 2.9 cm in width.

*Leaf color*.—Young upper surface; between 137B and 143A, young lower surface; 143A, mature upper surface; N137A, mature lower surface; 137B.

*Leaf surface*.—Upper and lower surface is slightly glossy and moderately to densely covered with very short strigose hairs; average length of 0.5 mm and NN155D in color.

*Petioles*.—Upper stem leaves nearly sessile, average length of stem leaves are 4.3 cm in length, v-shaped petiole is about 2.5 mm in length and 3 mm in width, color; upper and lower surfaces 144B, margins 143A, upper and lower surfaces smooth.

Flower description:

*Type*.—Terminal capitulum, heterogamous with ray florets around the head margin and disk florets in the center, forming a radiant head.

*Capitulum number*.—Up to 3 capitulae per main stem.

*Lastingness of inflorescence*.—About 10 days.

*Capitulum size*.—Matures to about 3.9 cm in height and 8.2 cm in diameter, disk size is an average of 3.1 cm in diameter.

*Fragrance*.—Faint and sweet fragrance.

*Involucral bracts or phyllary*.—About 60 arranged in 3 overlapping rows, up to 1 cm in length and 3 mm in width, dull in appearance, cuneate at base, acute apex, ovate to narrow ovate in shape, entire margins, lower surface and margins moderately to densely covered with very short hairs; 0.5 mm in length and NN155D in color, upper surface; smooth and 137B, base 143C in color, lower surface; 137A in color.

*Buds*.—Flattened globular in shape, immature ray florets near vertical, 3 cm in diameter and 1.9 cm in length, color; 141A, immature receptacle spines 23A, immature ray florets 59B to 59C.

*Peduncle*.—Strong, straight on top of main (flowering) stem, average angle of secondary peduncles 20°, terminal peduncle length is 11.9 and 5 mm in diameter, color; 147B to 148A, surface is densely covered with very short strigose hairs, 1 mm in length and NN155D in color.

*Ray florets*.—Rotate, about 31, oblanceolate in shape, about 1.9 cm in length and 3 cm in width, lobed to cleft apex, cuneate base, entire margin, slightly drooping in an average angle of 10° downward, upper surface texture is smooth and velvety and moderately ribbed lengthways (carinate), lower surface texture is smooth and moderately ribbed lengthways (carinate), color when opening upper surface; 60C, when opening lower surface; 59D, striped 59C, when fully open upper and lower surface; between 59D and 63B, upper and lower sides fading to 59D.

*Disk florets* (*bisexual*).—Numerous, about 400, tubular in shape, fused into tube upper 10% free, acute apex, base fused into tube, about 1.2 cm in length and 2 mm in width, entire margin, upper and lower surfaces smooth and glossy in appearance, color of upper and lower surfaces when opening; 143A, base 150B, color of upper and lower surfaces with fully open; 143B, base 144B to 144C, overall shape of disk head is flattened globose; 3.3 cm in height.

*Receptacle*.—Triangular in shape, about 9 mm in diameter and 1 cm in height, color is 155C.

*Receptacle spines*.—Average of 400, acicular in shape, acute apex, attenuate base, smooth and glossy surface, color: apex; 46A, mid-section; 25A to 25B, base; 145A; 1.2 cm in length.

Reproductive organs:

*Location of pistils and stamens*.—Disk florets only.

*Gynoecium*.—Pistil; 1, 1.2 cm in length, style; 9 mm in length and 145B in color, ovary; 145D in color.

*Androcoecium*.—Stamens; 4, filament 3 mm in length and 145C in color, anther; linear in shape, 5 mm in length and 200A to 202A in color, pollen is moderate to high in quantity and 17A in color.

*Fruit/seed*.—No fruit or seed detected to date.

It is claimed:

1. A new and distinct cultivar of *Echinacea* plant named 'Pipas' substantially as herein illustrated and described.

* * * * *